United States Patent
Yang

(10) Patent No.: US 7,211,459 B2
(45) Date of Patent: May 1, 2007

(54) FABRICATION METHOD OF AN ION SENSITIVE FIELD EFFECT TRANSISTOR

(75) Inventor: Chien-Sheng Yang, Taipei (TW)

(73) Assignee: AU Optronics Corp., Hsinchu (TW)

( * ) Notice: Subject to any disclaimer, the term of this patent is extended or adjusted under 35 U.S.C. 154(b) by 203 days.

(21) Appl. No.: 11/112,297

(22) Filed: Apr. 22, 2005

(65) Prior Publication Data
US 2005/0186697 A1    Aug. 25, 2005

Related U.S. Application Data

(62) Division of application No. 10/668,979, filed on Sep. 22, 2003, now abandoned.

(30) Foreign Application Priority Data
May 9, 2003    (TW) ................ 92112763 A

(51) Int. Cl.
*H01L 21/00*    (2006.01)
(52) U.S. Cl. .............. 438/49; 438/151; 257/253; 257/414
(58) Field of Classification Search ........... 257/253, 257/414; 438/49, 151, 161
See application file for complete search history.

(56) References Cited

U.S. PATENT DOCUMENTS

| | | | | |
|---|---|---|---|---|
| 6,236,075 B1 * | 5/2001 | Hsiung et al. | ............... | 257/252 |
| 6,387,724 B1 * | 5/2002 | Walker | ............... | 438/49 |
| 6,617,190 B2 * | 9/2003 | Chou et al. | ............... | 438/49 |
| 6,952,036 B2 * | 10/2005 | Suzuki et al. | ............... | 257/347 |
| 6,974,716 B2 * | 12/2005 | Hsiung et al. | ............... | 438/49 |
| 2002/0117694 A1 * | 8/2002 | Migliorato et al. | ............... | 257/253 |
| 2004/0072392 A1 | 4/2004 | Lin | ............... | 438/149 |
| 2004/0185591 A1 * | 9/2004 | Hsiung et al. | ............... | 438/49 |
| 2004/0222446 A1 * | 11/2004 | Yang | ............... | 257/253 |
| 2006/0035400 A1 * | 2/2006 | Wu et al. | ............... | 438/49 |
| 2006/0040420 A1 * | 2/2006 | Chou et al. | ............... | 438/49 |

FOREIGN PATENT DOCUMENTS

JP     2002-296229     * 10/2002

* cited by examiner

*Primary Examiner*—Zandra V. Smith
*Assistant Examiner*—Toniae M. Thomas
(74) *Attorney, Agent, or Firm*—Thomas, Kayden, Horstemeyer & Risley

(57) ABSTRACT

An ion sensitive field effect transistor (ISFET) and a fabrication method of the same are disclosed including a non-single-crystal silicon-base substrate, a polysilicon layer, a source, a drain, an insulating layer, a first electrode, a second electrode, a passivation layer, and an ion sensitive gate. The polysilicon layer is formed above the non-single-crystal silicon-base substrate, the source and the drain are formed in the polysilicon layer, and a predetermined channel region is formed in the polysilicon layer between the source and the drain. The insulating layer is formed above the polysilicon layer including a first contact hole and a second contact hole. The first electrode and the second electrode are electrically couple to the source and the drain by the first contact hole and the second contact hole, respectively. The passivation layer is formed above the insulating layer covering the first electrode and the second electrode, including an opening, which partially exposes the insulating layer above the predetermined channel region. The ion sensitive gate is formed in the opening above the insulating layer.

8 Claims, 4 Drawing Sheets

FABRICATION METHOD OF AN ION SENSITIVE FIELD EFFECT TRANSISTOR

This application is a divisional application of U.S. application Ser. No. 10/668,979, filed Sep. 22, 2003 now abandoned.

BACKGROUND OF THE INVENTION

1. Field of the Invention

The invention relates in general to a fabrication method of an ion sensitive field effect transistor (ISFET), and more particularly to a fabrication method of an ion sensitive field effect transistor (ISFET) having a non-single-crystal-silicon-base substrate.

2. Description of the Related Art

Ion sensitive field effect transistor (ISFET) is a chemical sensor that combines principles of electrochemistry and microelectronics. It is provided for contact with a to-be-measured solution and measuring a concentration of a particular ion thereof. The ISFET is developed on the basis of metal oxide semiconductor field effect transistor (MOSFET) and by the enhancement of the MOSFET. The difference between the ISFET and MOSFET is that a gate of the MOSFET is of metal gate, while the ISFET includes an ion sensitive gate for contact with a to-be-measured solution. An operation principle of the ISFET will be described in the later part. In addition, since the ISFET includes advantages of high input impedance, low output impedance, high response speed, and the like, and also the ISFET features that fabrication technique is compatible with the MOSFET, the ISFET is rich in incomparable development potential.

FIG. 1 is a cross-sectional view showing a conventional ion sensitive field effect transistor. The ion sensitive field effect transistor (ISFET) 100 includes a monocrystalline silicon substrate 102, a source 104, a drain 106, a silicon oxide layer 108, a first metal electrode 110a, a second metal electrode 110b, a passivation layer 112, and an ion sensitive gate 113. The monocrystalline silicon substrate 102 is of lightly doped P-type (P−), and also the monocrystalline silicon substrate includes a front side of the substrate 102a. A method of the ISFET 100 fabrication is as follows. After a predetermined doped-region of the front side of the substrate 102a is defined, a step of doping the monocrystalline silicon substrate 102 with N-type impurities from the front side of the substrate 102a forms the two separated source 104 and drain 106 of heavily doped N-type (N+) in the monocrystalline silicon substrate 102. The source 104 and the drain 106 are not as thick as the monocrystalline silicon substrate 102. A predetermined channel region 107 is formed in a region between the source 104 and the drain 106 in the monocrystalline silicon substrate 102, and also the predetermined channel region 107 is near the front side of the substrate 102a. In addition, a silicon oxide ($SiO_2$) layer 108 is formed on the front side of the substrate 102a, including a first contact hole 109a and a second contact hole 109b. Meanwhile, the first contact hole 109a and the second contact hole 109b partially expose the source 104 and the drain 106, respectively.

The first metal electrode 110a and the second metal electrode 110b are electrically couple to the source 104 and the drain 106 by the first contact hole 109a and the second contact hole 109b, respectively. And also the silicon oxide layer 108 is partially covered by the first metal electrode 110a and the second metal electrode 110b. The passivation layer 112 includes an opening 114 for exposing the silicon oxide layer 108 above the predetermined channel region 107. The ion sensitive gate 113 is formed above the silicon oxide layer 108 in the opening 113, which is provided for sensing ion concentration of a to-be-measured solution contained in the opening 114.

For example, when the opening 114 of the ISFET 100 is filled with a to-be-measured solution 202 containing positively charged ions, as shown in FIG. 2, the ion sensitive gate 113 will sense and measure the concentration of the positively charged ion in the solution 202, so that the ion sensitive gate 113 generates an interface variation of electric potential. At this time, under a circumstance of supplying a voltage difference Vds to the source 104 and the drain 106, there is also an electric current Ids flowing between the first metal electrode 110a and the second metal electrode 110b. Therefore, when there is the higher concentration of the positively charged ions in the solution 202, the ion sensitive gate 113 generates the more interface variation of electric potential. Comparatively, the electric current Ids flowing between the source 104 and the drain 106 would be larger. Consequently, the concentration of the positive ions in the to-be-measured solution 202 can be obtained.

One thing to note is that due to a pn-junction between the source 104 (N+), the drain 106 (N+), and the monocrystalline silicon substrate 102 (P−), an electric leakage phenomenon will occur. Thus, the measured electric current flowing between the first metal electrode 110a and the second metal electrode 110b is bias and not a substantial electric current. Therefore, there is a measurement error and the concentration of the positive ions in the to-be-measured solution 202 cannot be truly obtained. In addition, the monocrystalline silicon substrate 102 is very expensive, so as to increase a lot material cost.

SUMMARY OF THE INVENTION

In the light of the above-mentioned shortcomings, it is therefore an objective of the invention to provide a fabrication method of an ion sensitive field effect transistor (ISFET) A design of using a non-single-crystal silicon-base substrate can solve the conventional electric leakage phenomenon due to a pn-junction between the source (N+), the drain (N+), and the monocrystalline silicon substrate (P−). Besides, the non-single-crystal silicon-base substrate is not as expensive as the monocrystalline silicon substrate, as so to greatly reduce the material cost.

According to an objective of the invention, an ion sensitive field effect transistor (ISFET) is provided including a non-single-crystal silicon-base substrate, a polysilicon layer, a source, a drain, an insulating layer, a first electrode, a second electrode, a passivation layer, and an ion sensitive gate. The polysilicon layer is formed above the non-single-crystal silicon-base substrate, the source and the drain are formed in the polysilicon layer, and a predetermined channel region is formed in the polysilicon layer between the source and the drain. The insulating layer with a first contact hole and a second contact hole is formed above the polysilicon layer. The first electrode and the second electrode are electrically couple to the source and the drain by the first contact hole and the second contact hole, respectively. The passivation layer is formed above the insulating layer covering the first electrode and the second electrode. The passivation layer includes an opening, which partially exposes the insulating layer above the predetermined channel region. The ion sensitive gate is formed in the opening above the insulating layer.

According to another objective of the invention, a fabrication method of an ion sensitive field effect transistor (ISFET) is provided. First of all, a non-single-crystal silicon-base substrate is provided. Subsequently, a polysilicon layer is formed above the non-single-crystal silicon-base substrate. Next, a source and a drain are formed in the polysilicon layer, with a predetermined channel region formed in the polysilicon layer between the source and the drain. And then, an insulating layer is formed above the polysilicon layer including a first contact hole and a second contact hole. The first contact hole and the second contact hole partially expose the source and the drain, respectively. Accordingly, a first electrode and a second electrode are formed. The first electrode and the second electrode are electrically coupled with the source and the drain by the first contact hole and the second contact hole, respectively. And next, a passivation layer having an opening is formed above the insulating layer covering the first electrode and the second electrode, wherein the opening partially exposes the insulating layer above the predetermined channel region. Afterwards, an ion sensitive gate is formed in the opening above the insulating layer.

In addition, the non-single-crystal silicon-base substrate can be a glass substrate, a plastic substrate, or an insulation substrate, and the insulating layer is a silicon oxide (SiO2) layer. Moreover, the first electrode and the second electrode are two metal electrodes, and the passivation layer can be epoxy resin or other sealant resin substance.

Other objects, features, and advantages of the invention will become apparent from the following detailed description of the preferred but non-limiting embodiments. The following description is made with reference to the accompanying drawings.

DETAILED DESCRIPTION OF THE INVENTION

Accordingly, the invention particularly designs a fabrication method of an ion sensitive field effect transistor (ISFET) by using a non-single-crystal silicon-base substrate. It solves the conventional electric leakage phenomenon due to a pn-junction between the source (N+), the drain (N+), and the monocrystalline silicon substrate (P−). In addition, the non-single-crystal silicon-base substrate is not as expensive as the monocrystalline silicon substrate, as so to greatly reduce the cost of the material.

Figure 1:
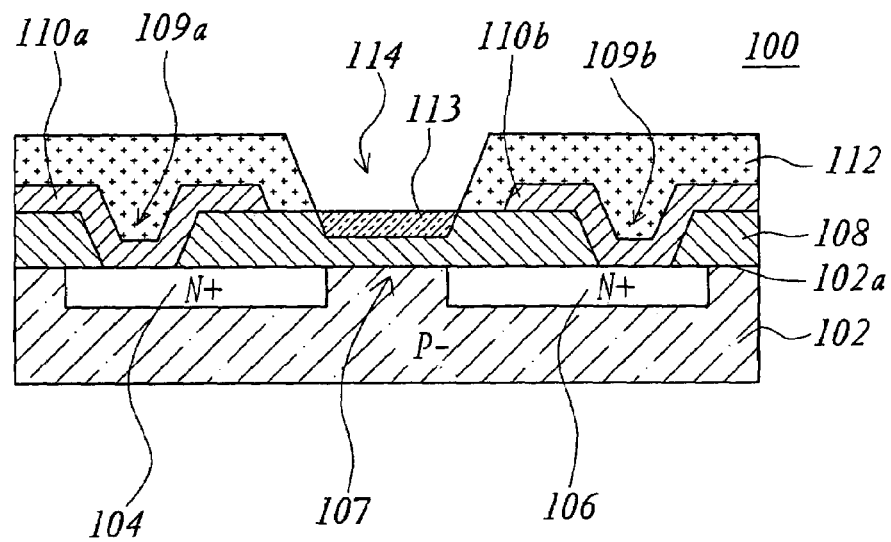
FIG. 1 (Prior Art) is a cross-sectional view showing a conventional ion sensitive field effect transistor (ISFET).
Figure 2:
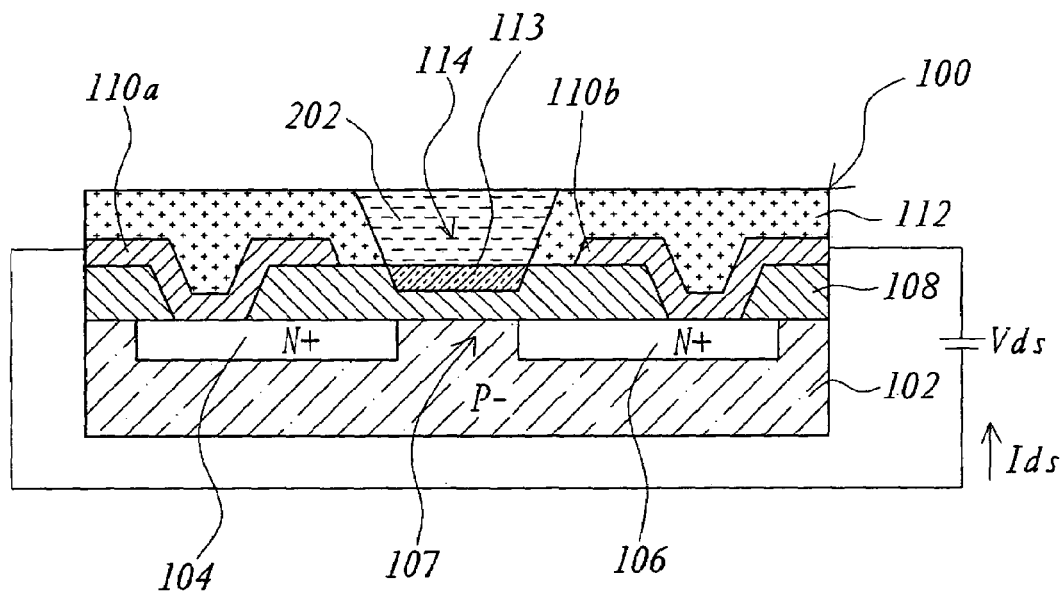
FIG. 2 (Prior Art) is a cross-sectional view showing a state of the conventional ion sensitive field effect transistor (ISFET) of the FIG. 1 measuring a positive ion concentration of a to-be-measured solution.
Figure 3:
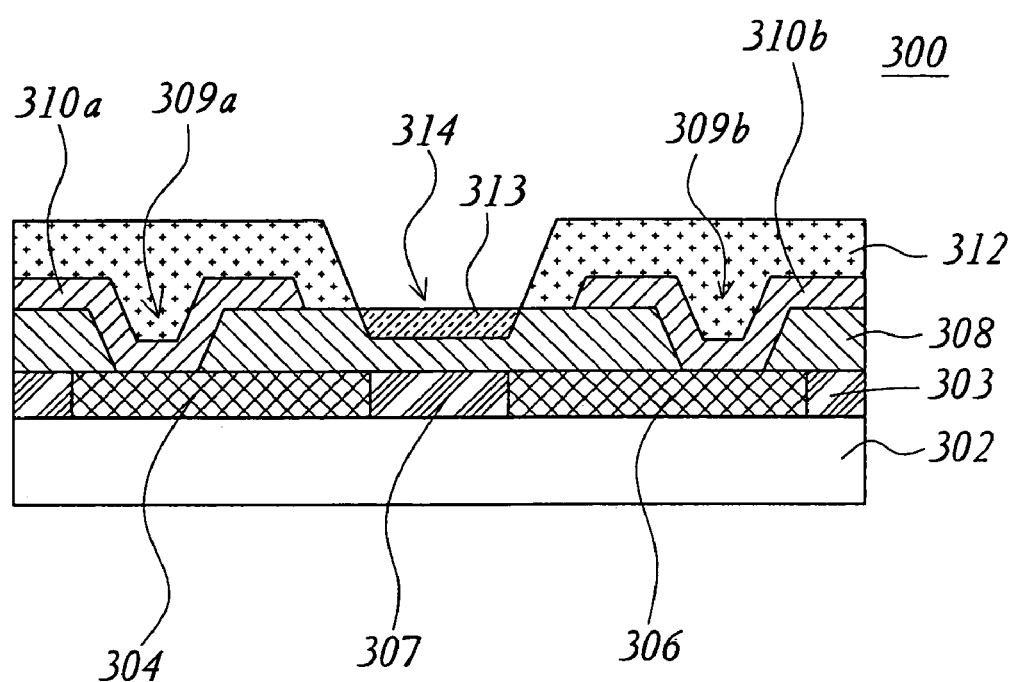
FIG. 3 is a schematic representation showing an ion sensitive field effect transistor (ISFET) of a preferred embodiment of the present invention.

FIG. 3 is a schematic representation showing an ion sensitive field effect transistor (ISFET) of a preferred embodiment of the present invention. The ion sensitive field effect transistor (ISFET) 300 in FIG. 3 includes a non-single-crystal silicon-base substrate 302, a polysilicon layer 303, a source 304, a drain 306, an insulating layer 308, a first electrode 310a, a second electrode 310b, a passivation layer 312, and an ion sensitive gate 313. The polysilicon layer 303 is formed above the non-single-crystal silicon-base substrate 302, the source 304 and the drain 306 are formed in the polysilicon layer 303, and a predetermined channel region 307 is formed in the polysilicon layer 303 between the source 304 and the drain 306. The insulating layer 308 is formed above the polysilicon layer 303 and has a first contact hole 309a and a second contact hole 309b.

The first electrode 310a and the second electrode 310b are electrically coupled to the source 304 and the drain 306 by the first contact hole 309a and the second contact hole 309b, respectively. And also the insulating layer 308 is partially covered by the first electrode 310a and the second electrode 310b. The passivation layer 312 is formed above the insulating layer 308 and covers the first electrode 310a and the second electrode 310b. The passivation layer 312 includes an opening 314, which partially exposes the insulating layer 308 above the predetermined channel region 307. The ion sensitive gate 313 is formed in the opening 314 above the insulating layer 308. The ion sensitive gate 313 serves to sense the ion concentration of the solution in the opening 314.

Figure 4A:
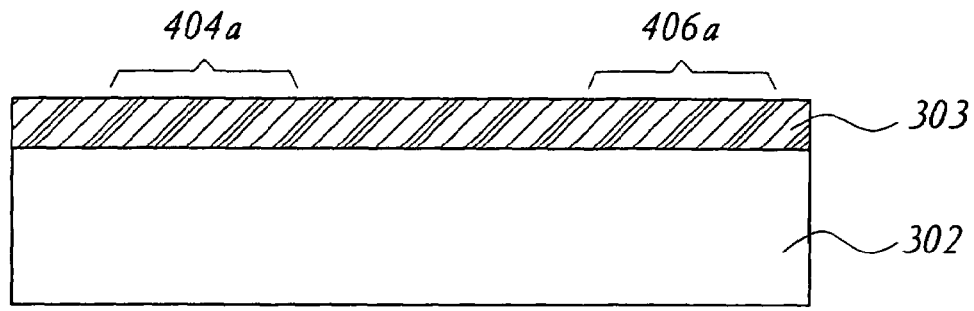
FIGS. 4A to 4D are schematic representations showing processes of a fabrication method of an ion sensitive field effect transistor (ISFET) according to a preferred embodiment of the present invention.
Figure 4B:
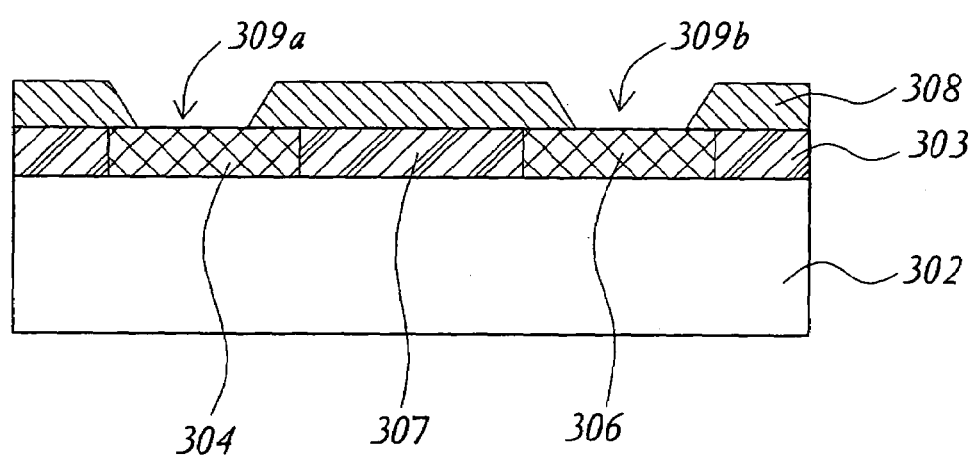

FIGS. 4A to 4D are schematic representations showing processes of a fabrication method of an ion sensitive field effect transistor (ISFET) according to a preferred embodiment of the present invention. First of all, referring to FIG. 4A, the non-single-crystal silicon-base substrate 302 is provided and also the polysilicon layer 303 is formed above the non-single-crystal silicon-base substrate 302. Subsequently, a front side of the polysilicon layer 303 is defined so as to form a first predetermined doped-region 404a and a second predetermined doped-region 406a. And then the first predetermined doped-region 404a and the second predetermined doped-region 406a are doped, so that the source 304 and the drain 306 are formed correspondingly in the polysilicon layer 303. The predetermined channel region 307 is formed in a region between the source 304 and the drain 306 in the polysilicon layer 303, as shown in FIG. 4B. Referring to FIG. 4B, the insulating layer 308 is formed above the polysilicon layer 303 and has a first contact hole 309a and a second contact hole 309b. The first contact hole 309a and the second contact hole 309b expose a part of the source 304 and the drain 306, respectively.

Figure 4C:
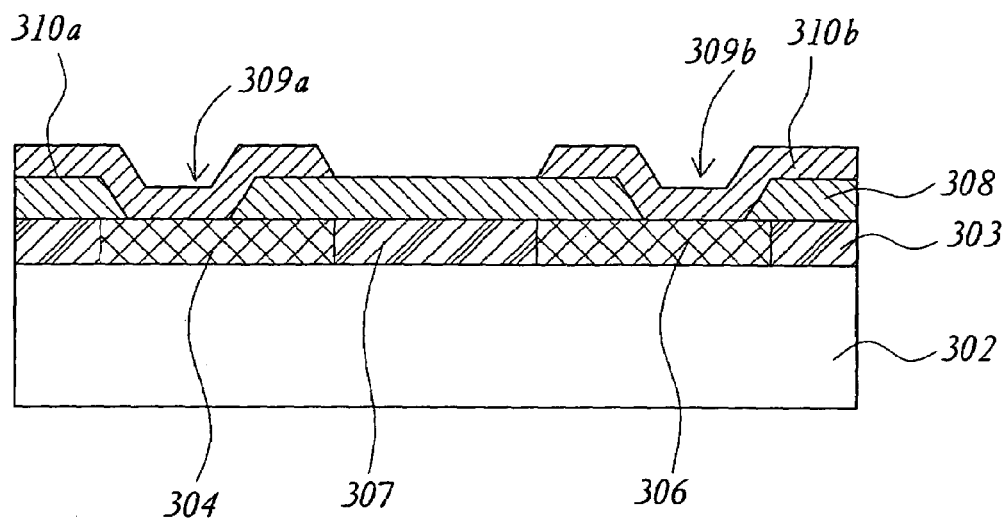
Figure 4D:
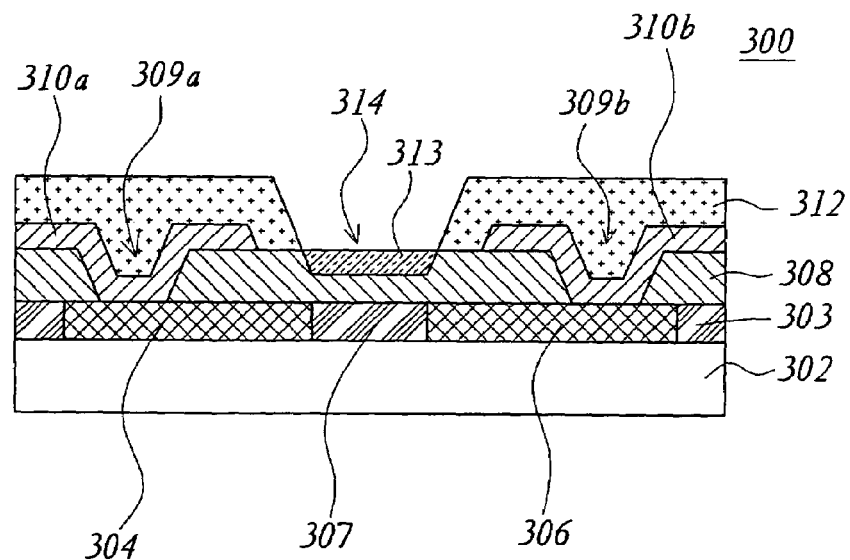

Accordingly, the first electrode 310a and the second electrode 310b are formed. The first electrode 310a and the second electrode 310b are electrically coupled to the source 304 and the drain 306 by the first contact hole 309a and the second contact hole 309b, respectively. And also the insulating layer 308 is partially covered by the first electrode 310a and the second electrode 310b, as shown in FIG. 4C. And then, the passivation layer 312 with the opening 314 is formed above the insulating layer 308 and covers the first electrode 310a and the second electrode 310b. The opening 314 exposes a part of the surface of the insulating layer 308 above the predetermined channel region 307. And next, the ion sensitive gate 313 is formed in the opening 314 above the insulating layer 308, as shown in FIG. 4D, so as to obtain the ion sensitive field effect transistor (ISFET) 300 of the present invention accordingly.

While the invention has been described by way of example and in terms of a preferred embodiment, it is to be understood that the technique of the invention is not limited thereto. For example, the non-single-crystal silicon-base substrate 302 can be a glass substrate, a plastic substrate, or an insulation substrate, and the insulating layer 308 is a silicon oxide (SiO$_2$) layer or other insulating substance. Moreover, the first electrode 310a and the second electrode 301b are two metal electrodes, and the passivation layer 312 can be epoxy resin or other sealant resin substance. Further, the source 304 and the drain 306 can be heavily doped as N-type (N+), while the polysilicon layer 303 can be lightly doped as P-type (P−).

Accordingly, the ion sensitive field effect transistor (ISFET) and the fabrication method thereof of the preferred embodiment of the invention as disclosed above by using a non-single-crystal silicon-base substrate is provided. It can solve the conventional electric leakage phenomenon due to a pn-junction between the source (N+), the drain (N+), and the monocrystalline silicon substrate (P−). In addition, the non-single-crystal silicon-base substrate is not as expensive as the monocrystalline silicon substrate, as so to greatly reduce the material cost.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A fabrication method of an ion sensitive field effect transistor (ISFET) comprising:

providing a non-single-crystal silicon-base substrate;

forming a polysilicon layer above the non-single-crystal silicon-base substrate;

forming a source and a drain in the polysilicon layer, with a predetermined channel region formed between the source and the drain in the polysilicon layer;

forming an insulating layer with a first contact hole and a second contact hole above the polysilicon layer, wherein the first contact hole and the second contact hole partially expose the source and the drain exposed, respectively;

forming a first electrode and a second electrode, wherein the first electrode and the second electrode are electrically coupled with the source and the drain by the first contact hole and the second contact hole, respectively;

forming a passivation layer with an opening above the insulating layer, wherein the passivation layer covers the first electrode and the second electrode, and the opening partially exposes the insulating layer above the predetermined channel region; and forming an ion sensitive gate in the opening above the insulating layer.

2. The method according to claim 1, wherein the step of forming a source and a drain in the polysilicon layer further comprises:

defining a front side of the polysilicon layer so as to form two predetermined doped-regions;

doping the two predetermined doped-regions so as to form the source and the drain correspondingly.

3. The method according to claim 1, wherein the non-single-crystal silicon-base substrate is a glass substrate.

4. The method according to claim 1, wherein the non-single-crystal silicon-base substrate is a plastic substrate.

5. The method according to claim 1, wherein the non-single-crystal silicon-base substrate is an insulation substrate.

6. The method according to claim 1, wherein the insulating layer is a silicon oxide layer.

7. The method according to claim 1, wherein the first electrode and the second electrode are two metal electrodes.

8. The method according to claim 1, wherein the passivation layer is epoxy resin.

* * * * *